United States Patent [19]

Schönafinger et al.

[11] Patent Number: 5,155,109

[45] Date of Patent: Oct. 13, 1992

[54] 3-PIPERAZINOSYDNONE IMINES, PROCESS FOR THEIR PREPARATION AND THEIR USE

[75] Inventors: Karl Schönafinger, Alzenau; Helmut Bohn, Schöneck; Melitta Just, Langen, all of Fed. Rep. of Germany

[73] Assignee: Cassella Aktiengesellschaft, Frankfurt am Main, Fed. Rep. of Germany

[21] Appl. No.: 730,491

[22] Filed: Jul. 16, 1991

[30] Foreign Application Priority Data

Oct. 4, 1990 [DE]  Fed. Rep. of Germany ....... 4031373

[51] Int. Cl.$^5$ ................. A61K 31/495; C07D 413/04
[52] U.S. Cl. ..................................... 514/252; 544/367
[58] Field of Search ......................... 544/367; 514/252

[56] References Cited

U.S. PATENT DOCUMENTS

| | | | |
|---|---|---|---|
| 4,430,342 | 2/1984 | Hidaka et al. | 544/367 |
| 4,436,743 | 3/1984 | Scho afinger et al. | 544/367 |
| 4,452,797 | 6/1984 | Scho afinger et al. | 544/367 |
| 4,937,244 | 6/1990 | Scho afinger et al. | 544/367 |

FOREIGN PATENT DOCUMENTS

| | | |
|---|---|---|
| 108241 | 6/1986 | European Pat. Off. . |
| 3526068 | 1/1987 | Fed. Rep. of Germany . |
| 3702083 | 8/1988 | Fed. Rep. of Germany . |

Primary Examiner—Cecilia Tsang
Attorney, Agent, or Firm—Perman & Green

[57] ABSTRACT

The invention relates to pharmacologically active substituted 3-aminosydnone imines of the general formula I

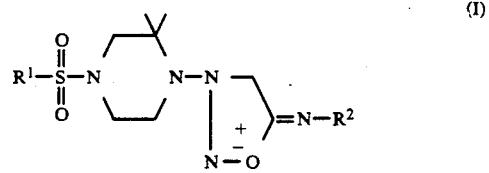

in which $R^1$ denotes $(C_1-C_4)$-alkyl, di-$(C_1-C_4)$-alkylamino or $(C_6-C_{12})$-aryl, which can optionally be substituted by $(C_1-C_4)$-alkyl;

$R^2$ denotes hydrogen or $COR^3$ and $R^3$ denotes $(C_1-C_4)$-alkyl, $(C_1-C_4)$-alkoxy, $(C_1-C_4)$-alkoxy-$(C_1-C_4)$-alkyl, acetoxy-$(C_1-C_4)$-alkyl, $(C_6-C_{12})$-aryl, which can be substituted by $(C_1-C_4)$-alkyl or $(C_1-C_4)$-alkoxy, pyridyl, pyridyl$(C_1-C_4)$alkyl or $(C_3-C_8)$-cycloalkyl and their pharmacologically acceptable acid addition salts.

5 Claims, No Drawings

3-PIPERAZINOSYDNONE IMINES, PROCESS FOR THEIR PREPARATION AND THEIR USE

The invention relates to pharmacologically active substituted 3-aminosydnone imines of the general formula I

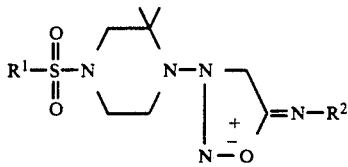
(I)

in which $R^1$ denotes $(C_1-C_4)$-alkyl, di-$(C_1-C_4)$-alkylamino or $(C_6-C_{12})$-aryl, which can optionally be substituted by $(C_1-C_4)$-alkyl;

$R^2$ denotes hydrogen, or $COR^3$ and $R^3$ denotes $(C_1-C_4)$-alkyl, $(C_1-C_4)$-alkoxy, $(C_1-C_4)$-alkoxy-$(C_1-C_4)$-alkyl, acetoxy-$(C_1-C_4)$-alkyl, $(C_6-C_{12})$-aryl, which can be substituted by $(C_1-C_4)$-alkyl or $(C_1-C_4)$-alkoxy, pyridyl, pyridyl$(C_1-C_4)$alkyl or $(C_3-C_8)$-cycloalkyl and their pharmacologically acceptable acid addition salts.

The invention furthermore relates to a process for the preparation of the compounds according to the invention and to their use.

Alkyl radicals, alkoxy radicals, alkoxyalkyl radicals, acetoxyalkyl radicals and dialkylamino radicals may be straight-chain or branched. This also applies if they occur as substituents of aryl or pyridyl.

$(C_1-C_4)$Alkyl radicals may be: methyl, ethyl, n-propyl, i-propyl, n-butyl, i-butyl, tert.-butyl and sec.-butyl.

Alkoxy, alkoxyalkyl, acetoxyalkyl, dialkylamino and pyridylalkyl radicals are derived from the said alkyl radicals.

$(C_3-C_8)$-Cycloalkyl radicals are in particular cyclopentyl and cyclohexyl.

$(C_6-C_{12})$-Aryl is in particular phenyl, substituted $(C_6-C_{12})$-aryl is in particular p-tolyl and p-methoxyphenyl. Pyridyl is in particular 3-pyridyl, pyridylalkyl is in particular 3-pyridylalkyl.

$R^1$ preferably denotes methyl, p-tolyl or dimethylamino.

$R^3$ preferably denotes ethyl, i-propyl, tert-butyl, ethoxy, pyridyl, p-methoxyphenyl or cyclohexyl.

A compound of the general formula I can be prepared by cyclising a compound of the general formula II

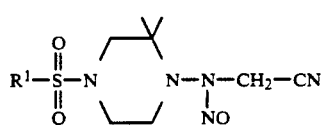
(II)

in which R' is as defined above, to give a compound of the general formula Ia

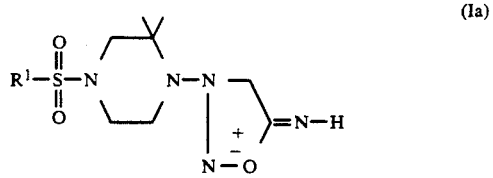
(Ia)

and in the case in which it is intended to prepare a compound of the formula I where $R^2 = -COR^3$, by acylating this compound or an acid addition salt thereof with an acylating agent which introduces the radical $-COR^3$, and optionally converting the compound thus obtained into a pharmacologically acceptable acid addition salt.

The cyclisation of the compound II to give the compound Ia is carried out in a suitable organic or inorganic solvent, dispersant or diluent with the addition of a cyclising agent, normally at temperatures from $-10°$ to $40°$ C., in particular 0 to $40°$ C., preferably at $0°$ to $20°$ C.

Suitable cyclising agents are those which establish a pH below 3 in aqueous solution, that is to say, for example, mineral acids, such as sulphuric, nitric or phosphoric acid, preferably hydrogen chloride, but also strong organic acids, such as trifluoroacetic acid. The cyclisation is normally carried out with ice-cooling.

0.1 to 10 mol, preferably 1 to 5 mol, of the cyclising agent is used, for example, relative to 1 mol of the compound of the formula II. The cyclising agent is normally employed in excess. The use of hydrogen chloride as a cyclising agent is particularly advantageous, and it is normally passed into the reaction mixture. The corresponding acid addition salt of the compound Ia is normally obtained in the cyclisation.

Suitable solvents, dispersants or diluents are, for example: alcohols, for example those having 1 to 8 C atoms, in particular those having 1 to 6 C atoms, preferably those having 1 to 4 C atoms, such as, for example, methanol, ethanol, i- and n-propanol, i-, sec- and tert-butanol, n-, i-, sec- and tert-pentanol, n-hexanol, 2-ethylbutanol, 2-ethylhexanol, isooctyl alcohol, cyclopentanol, cyclohexanol, methylcyclohexanol (mixture) and benzyl alcohol; ethers, in particular those having 2 to 8 C atoms in the molecule, such as, for example, diethyl ether, methyl ethyl ether, di-n-propyl ether, di-isopropyl ether, methyl n-butyl ether, methyl tert-butyl ether, ethyl propyl ether, di-butyl ether, tetrahydrofuran, 1,4-dioxane, 1,2-dimethoxyethane and bis-$\beta$-methoxyethyl ether; oligoethylene glycol dimethyl ethers, such as, for example, tetraglyme or pentaglyme; alkyl carboxylates, in particular those having 2 to 10 C atoms in the molecule, such as, for example, methyl, ethyl, butyl or isobutyl formate, methyl, ethyl, propyl, isopropyl, butyl, isobutyl or sec-butyl, amyl, isoamyl, hexyl, cyclohexyl or benzyl acetate or methyl, ethyl or butyl propionate; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, methylcyclohexanone, dimethylcyclohexanone, benzophenone and acetophenone; aliphatic hydrocarbons, such as, for example, hexane and heptane, low- and high-boiling petroleum ethers, petroleum spirits and white spirit; cycloaliphatic hydrocarbons, such as, for example, cyclopentane, cyclohexane, methylcyclohexane, tetralin and decalin; aromatic hydrocarbons, such as, for example, benzene, toluene, o-, m- and p-xylene, and ethylbenzene; halogenated aliphatic or aromatic hydrocarbons, such as, for example, methylene chloride, chloroform, carbon tetrachloride, 1,2-dichloroethane, chlorobenzene and dichlorobenzene; hexamethylphosphoramide; sulphoxides, such as, for example, dimethyl sulphoxide; tetramethylene sulphone; and water. Mixtures of different solvents or dispersants may also be used, for example water-methanol or, preferably, ethyl acetatemethanol.

The compound of the formula Ia is the compound of the general formula I according to the invention in the case in which $R^2$=hydrogen.

The acylation of the compound of the formula Ia, which may also be present in the form of an acid addition salt, in order to introduce the radical $R^2$=—$COR^3$ can be carried out in a manner known per se using a suitable acylating agent of the formula III

(III)

in which X represents a radical which can be eliminated nucleophilically.

In the formula III, X, for example, in particular denotes halogen, preferably —Cl or —Br; —OH; —O-alkyl, in particular having 1 to 5 C atoms; —O-aryl, the aryl radical in particular being a phenyl radical which may also be mono- or polysubstituted by alkyl, in particular methyl, and/or nitro, and is, for example, a tolyl, dinitrophenyl or nitrophenyl radical; —O—CO—$R^3$; —O—CO—O-alkyl, in particular having 1 to 5 C atoms in the alkyl radical, or the radical of an azole or benzazole which has at least 2 N atoms in the quasi-aromatic 5-membered ring and is bonded via an N atom.

The acylation is expediently carried out in a liquid or liquid disperse phase in the presence of an inert solvent, dispersant or diluent or in an excess of the acylating agent, expediently with stirring.

In the acylation, the molar ratio between the compound of the formula Ia and the acylating agent of the formula III is theoretically 1:1. However, the acylating agent can also be employed in excess or in a sub-equivalent amount. The acylating agent of the formula III is expediently employed in excess. Excesses of up to 50 mol% are usually sufficient, i.e. the molar ratio between the compound of the formula Ia and the acylating agent of the formula III is normally 1:(1 to 1.5), preferably 1:(1 to 1.2). If an acid is eliminated in the acylation reaction, the addition of an acid scavenger, such as, for example, an alkali metal hydroxide, such as, for example, sodium hydroxide, potassium hydroxide or lithium hydroxide, a tertiary organic amine, such as, for example, pyridine or triethylamine, an alkali metal carbonate or alkali metal bicarbonate, such as, for example, sodium carbonate or sodium bicarbonate, or an alkali metal salt of a weak organic acid, such as, for example, sodium acetate, is expedient. Suitable catalysts, such as, for example, 4-dimethylaminopyridine, may also be added during the acylation reaction.

The acylation may in principle be carried out at temperatures between −10° C. and the boiling point of the solvent, dispersant or diluent used. In many cases, the reaction is carried out at 0° to 50° C., in particular at 0° to 30° C. and preferably at room temperature.

The compounds of the formula III are acylating agents and thus represent, for example: for X=halogen: acid halides or haloformic acid esters, of which acid chlorides and chloroformic acid esters are preferred; for —OH: carboxylic acids; for —O-alkyl and —O-aryl: esters, of which the tolyl, 2,4-dinitro- or 4-nitrophenyl esters are preferred; for —O—CO—$R^3$: anhydrides; for —O—CO—O-alkyl: mixed carboxylic acid/carbonic acid anhydrides; or heterocyclic amides or azolides, in particular of N,N'-carbonyldiazoles, such as, for example, N,N'-carbonyldiimidazole, 2,2'-carbonyl-1,2,3-ditriazole, 1,1'-carbonyl-1,2,4-ditriazole, N,N'-carbonyldipyrazole and 2,2'-carbonylditriazole (compare, for example, H. A. Staab, M. Lücking and F. H. Dürr, Chem. Ber. 95, (1962), 1275 et seq., H. A. Staab and A. Mannschreck, Chem. Ber. 95, (1962), 1284 et seq.; H. A. Staab and W. Rohr, "Synthesen mit heterocyclischen Amiden (Azoliden)" [Syntheses with heterocyclic amides (azolides)]in "Neuere Methoden der Präparativen Organischen Chemie" [Newer methods of preparative organic chemistry], volume V, Verlag Chemie, 1967, p. 53 et seq., in particular pp. 65 to 69). The acylating agents of the formula III can be prepared by processes which are known per se.

When using a carboxylic acid as the acylating agent, the addition of an activating agent which has the object of increasing or of activating the acylating potential of the carboxylic acid or of converting the carboxylic acid into a reactive carboxylic acid derivative of the formula III in situ or preferably shortly before the reaction with the compound of the formula Ia is expedient. Suitable activating agents of this type are, for example: N,N'-disubstituted carbodiimides, in particular if they contain at least one secondary or tertiary alkyl radical, such as, for example, diisopropyl-, dicyclohexyl- or N-methyl-N'-tert.-butylcarbodiimide (compare Methodicum Chimicum, Verlag G. Thieme, Stuttgart, Vol. 6, (1974), pp. 682/683, and Houben-Weyl, Methoden der Org. Chemie [Methods of organic chemistry], Vol. 8, (1952), pp. 521/522); carbonic acid derivatives, such as, for example, phosgene; chloroformic acid esters, in particular having 1 to 5 C atoms in the alkyl radical (compare, for example, Tetrahedron Letters 24 (1983), 3365 to 3368); carbonic acid esters, such as, for example, N,N'-disuccinimidyl carbonate, diphthalimidyl carbonate, 1,1'-(carbonyldioxy)dibenzotriazole or di-2-pyridyl carbonate (compare, for example, Tetrahedron Letters, Vol. 25, No. 43, 4943–4946), if desired in the presence of suitable catalysts, such as, for example, 4-dimethylaminopyridine. In addition, N,N'-carbonyldiazoles, such as, for example, N,N'-carbonyldiimidazole, 2,2'-carbonyl-1,2,3-ditriazole, 1,1'-carbonyl-1,2,4-ditriazole, N,N'-carbonyldipyrazole, 2,2'-carbonylditetrazole, N,N'-carbonylbenzimidazole or N,N'-carbonylbenzotriazole are suitable as activating agents (compare, for example, H. A. Staab, M. Lücking and F. H. Dürr, loc. cit; H. A. Staab and A. Mannschreck loc. cit.; H. A. Staab and W. Rohr loc. cit). The N,N'-carbonyldiazole used is frequently the commercially available N,N'-carbonyldiimidazole. However, the other N,N'-carbonylazoles are also easily accessible from the respective azole and phosgene.

In addition, suitable activating agents for carboxylic acids are: derivatives of oxalic acid, such as, for example, oxalyl chloride (compare, for example, GB Patent Specification 2,139,225) or N,N'-oxalyldiazoles, such as, for example, 1,1'-oxalyldiimidazole, 1,1'-oxalyldi-1,2,4-triazole and 1,1'-oxalyldi-1,2,3,4-tetrazole (compare, for example, Shizuaka Murata, Bull. Chem. Soc. Jap. 57, 3597–3598 (1984)); methylethylphosphinic anhydride (compare, for example, German Offenlegungsschrift 3,101,427); diphosphorus tetraiodide (Chem. Lett. 1983, 449); dialkyl disulphite (Indian J. Chem. 21, 259 (1982)); or other reactive agents.

Suitable solvents, dispersants or diluents are, for example, those which have been mentioned for carrying out the cyclisation, and moreover also, for example, pyridine and amides, such as, for example, dimethylformamide. In addition to water, polar organic solvents, such as dimethylformamide, dimethyl sulphoxide or pyridine, are preferred for the acylation. Solvent mixtures, such as, for example, a mixture of water and methylene chloride, are also suitable.

The compounds of the general formula I can form acid addition salts with inorganic or organic acids. For the formation of pharmacologically acceptable acid addition salts, suitable acids are, for example: hydrogen chloride, hydrogen bromide, naphthalene-disulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. The acid addition salts may be prepared in a customary manner by combining the components, expediently in a suitable solvent or diluent.

In the synthesis of the compounds of the general formula Ia, the acid addition salts are normally obtained.

The starting compound of the general formula II may be prepared in a simple manner known per se by Strecker's aminonitrile synthesis from compounds of the general formula IV

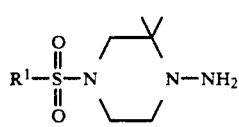

in which R' is as defined above, by reaction with formaldehyde and hydrocyanic acid or sodium cyanide in a suitable solvent, for example water, a compound of the general formula V

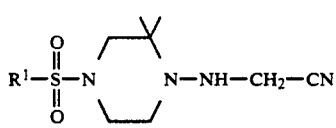

first being formed, which is converted by nitrosylation into the compound II. The nitrosylation is carried out in a known manner in a suitable solvent, preferably in water, for example at temperatures of 0° to 10° C. The nitrous acid is in this case normally generated from an alkali metal nitrite, for example sodium nitrite, and hydrochloric acid. It is expedient to adjust the aqueous solution of the compound V to a pH of 1 to 3 with hydrochloric acid and to add the alkali metal nitrite dropwise in the form of an aqueous solution to the stirred and cooled solution of the compound.

The solution of the compound II obtained here can be subjected directly to the cyclisation reaction. However, normally it is appropriate to take up the nitroso compound II in a suitable organic solvent first and to carry out the cyclisation to give the compound of the formula Ia in it, if desired after addition of a further solvent.

The compounds of the general formula IV can be prepared, starting from compounds of the general formula VI

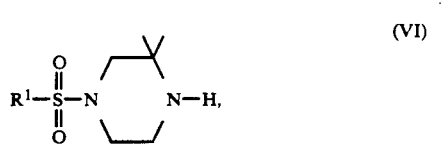

by either
a) nitrosylating a compound of the formula VI to give the N-nitroso compound VII and then reducing

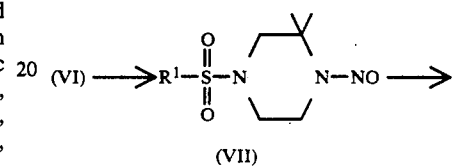

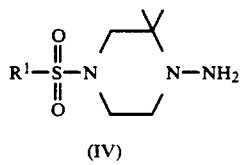

or, in a manner known per se, b) converting a compound of the general formula VI into the urea derivative VIII with an alkali metal cyanate in acidic medium, and then reacting by the Hoffmann degradation to give the compound IV:

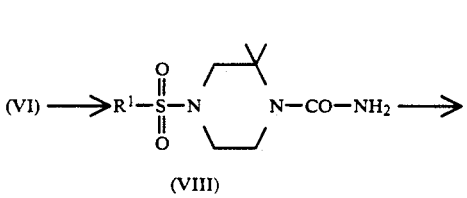

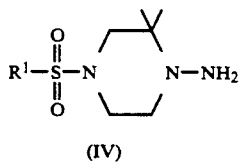

The nitrosylation of the compound of the general formula VI to give the compound of the general formula VII is carried out analogously to the abovementioned process, and the subsequent reduction is carried out in a manner known per se, preferably using thiourea dioxide.

Urea synthesis by reaction of an amine with an alkali metal cyanate in acidic aqueous solution (i.e. reaction of the compound of the general formula VI to give the compound of the general formula VIII) is known and described in the literature (see, for example, Houben-Weyl, Methoden der Organischen Chemie (Methods of Organic Chemistry), 4th Edition, Vol. E4, page 362). A preferred alkali metal cyanate here is potassium cyanate. The Hoffmann degradation, i.e. the synthesis of an amine from the corresponding amide by reaction with hypochlorite or hypobromite, is also known from the literature (see, for example, Houben-Weyl, Methoden der Organischen Chemie (Methods of Organic Chemistry), 4th Edition, Vol. XI/1 pages 854 et seq.).

The compounds of the general formula VI are prepared in a manner known per se by reaction of the known 2,2-dimethylpiperazine with the known sulfonyl chlorides $R^1$—$SO_2$—Cl.

The compounds of the general formula I and their pharmacologically acceptable acid addition salts have useful pharmacological properties. Their action on the cardiovascular system is particularly pronounced. Compared with known sydnone imine compounds substituted in the 3-position, for example those of EP-B-59,356 and the commercially available structurally similar compound molsidomin, they surprisingly have a greater and longer duration of action. For example, they lower the blood pressure as well as the pulmonary artery pressure and the left ventricular end-diastolic pressure and thus contribute to a relief of the load on the heart in the sense of an antianginal action, without provoking reflex tachycardia at the same time.

The compounds can additionally exhibit antithrombotic effects as a result of inhibition of platelet aggregation.

The compounds of the formula I and their pharmacologically acceptable acid addition salts can therefore be administered to humans as medicaments by themselves, in mixtures with one another or in the form of pharmaceutical preparations which permit enteral or parenteral use and which contain as the active component an effective dose of at least one compound of the formula I or an acid addition salt thereof, in addition to customary pharmaceutically innocuous excipients and additives.

The medicaments can be administered orally, for example in the form of pills, tablets, film tablets, coated tablets, hard and soft gelatin capsules, solutions, syrups, emulsions or suspensions, or aerosol mixtures. Administration may, however, also be carried out rectally, for example in the form of suppositories, or parenterally, for example in the form of injection solutions, or percutaneously, for example in the form of ointments or tinctures.

The pharmaceutical preparations can be prepared using pharmaceutically inert inorganic or organic excipients. For the preparation of pills, tablets, coated tablets and hard gelatin capsules, for example lactose, maize starch or derivatives thereof, talc, stearic acid or its salts can be used. Excipients for soft gelatin capsules and suppositories are, for example, fats, waxes, semi-solid and liquid polyols, natural or hardened oils etc. Suitable excipients for the preparation of solutions and syrups are, for example, water, sucrose, dextrose, glucose, polyols, etc. Suitable excipients for the preparation of injection solutions are, for example, water, alcohols, glycerol, polyols or vegetable oils.

The pharmaceutical preparations may contain, in addition to the active compounds and excipients, further additives, such as, for example, fillers, extenders, disintegrants, binders, glidants, wetting agents, stabilisers, emulsifiers, preservatives, sweeteners, colourings, flavourings or aromatisers, buffer substances, and in addition solvents or solubilisers or agents for achieving a depot effect, as well as salts for changing the osmotic pressure, coating agents or antioxidants. They may also contain two or more compounds of the formula I or their pharmacologically acceptable acid addition salts and also other therapeutically active substances.

Examples of other therapeutically active substances of this type are: $\beta$-receptor blockers, such as, for example, propranolol, pindolol, metoprolol; vasodilators, such as, for example, carbochromen; tranquilisers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, ramipril, prazosine, clonidine, Rauwolfia alkaloids; agents which lower the fatty acid level in the blood, such as, for example, bezafibrate, fenofibrate; and agents for thrombosis prophylaxis, such as, for example, phenprocoumon.

The compounds of the formula I, their pharmacologically acceptable acid addition salts and pharmaceutical preparations which contain the compounds of the formula I or their pharmacologically acceptable acid addition salts as active compounds can be used in humans for control or prevention of diseases of the cardiovascular system, for example as antihypertensive medicaments in the various forms of high blood pressure, and in control or prevention of angina pectoris etc. The dosage may vary within wide limits and is to be suited to the individual requirements in each individual case. In general, a daily dose of about 0.5 to 100 mg, preferably 1 to 20 mg, per human individual is suitable for oral administration. For other administration forms, the daily dose, owing to the good absorption of the active compounds, is also in similar amount ranges, i.e. in general also 0.5 to 100 mg/human. The daily dose is normally divided into several, for example 2 to 4, part administrations.

The pharmacological action of the compounds of the formula I was determined by a modified method of Godfraind and Kaba (Arch. Int. Pharmacodyn. Ther. 196, (Suppl) 35 to 49, 1972) and of Schüman et al. (Naunyn-Schmiedeberg,s Arch. Pharmacol. 289, 409 to 418, 1975). In this connection, spiral strips of the pulmonary artery of the guinea-pig are depolarised with 40 mmol/l of potassium after equilibration in calcium-free Tyrode solution. An addition of 0.5 mmol/l of $CaCl_2$ then induces a contraction.

The relaxing action of the test substance is determined by cumulative addition in 1/2 log 10 stepped concentrations. From the concentration-effect curve (abscissa: -log mol/l of test substance, ordinate: % inhibition of the maximum contraction, average value of 4 to 6 vessel strips), the concentration of the test substance is determined which inhibits the contraction by 50% (=$IC_{50}$, mol/l). The duration of action of the test substance is given by the time which is needed after the addition of the test substance until the starting value is obtained again. The values thus obtained are indicated in the following table. As the comparison with the $IC_{50}$ values for the known compound molsidomine (cf. DE-B-1,695,897) shows, the values for the compounds of the general formula I are considerably more favourable. On the other hand, the similarly active compound SIN-1 is clearly surpassed by the compounds according to the invention with respect to its duration of action.

$$R^1-\underset{\underset{O}{\|}}{\overset{\overset{O}{\|}}{S}}-N\underbrace{\diagup\diagdown}_{\diagdown\diagup}N-N\underset{\underset{N-O}{|}}{\diagdown}\!\!\!\!\!\!\!\overset{+}{\diagup}\!\!=N-R^2$$

| R¹ | R² | IC$_{50}$ (in mol/l) | Duration of action (min) |
|---|---|---|---|
| —CH$_3$ | —H | $1.9 \cdot 10^{-6}$ | 200 |
| ![]—⟨C$_6$H$_4$⟩—CH$_3$ | —H | $6.5 \cdot 10^{-7}$ | 220 |
| —N(CH$_3$)$_2$ | —H | $2.5 \cdot 10^{-6}$ | 200 |
| —CH$_3$ | —C(O)—CH(CH$_3$)$_2$ | $3 \cdot 10^{-6}$ | 210 |
| Molsidomine | | $3 \cdot 10^{-4}$ | 100 |
| SIN-1 | | $1 \cdot 10^{-6}$ | 80 |

Molsidomine: N-Ethoxycarbonyl-3-morpholinosydnone imine
SIN-1: 3-Morpholinosydnone imine hydrochloride (Linsidomine)

EXAMPLES

1.
3-(2,2-Dimethyl-4-methanesulphonylpiperazin-1-yl)sydnone imine hydrochloride a) 4-Methanesulphonyl-2,2-dimethylpiperazine

A solution of 52.8 g of methanesulphonyl chloride in 100 ml of toluene is added dropwise to a mixture of 52.6 g of 2,2-dimethylpiperazine, 69.9 g of potassium carbonate and 150 ml of toluene, the internal temperature rising to about 55° C. After a stirring time of 3 hours, the insoluble fraction is filtered off with suction and the toluene solution is evaporated in vacuo. The oil which remains gradually solidifies and is recrystallised from isopropanol for purification.

Yield: 51.2 g, m.p.: 103°–6° C.

b) 4-Methanesulphonyl-2,2-dimethyl-1-nitrosopiperazine

A mixture, cooled to 0°–5° C., of 45 g of 4-methanesulphonyl-2,2-dimethylpiperazine, 19.3 g of sodium nitrite, 250 ml of water and 100 ml of methanol is adjusted to pH 1.0 using conc. HCl and stirred at a gradually increasing temperature for 12 hours. The precipitate is filtered off with suction, washed with water and dried in vacuo.

Yield: 45 g, M.p.: 158°–61° C.

c) 1-Amino-4-methanesulphonyl-2,2-dimethylpiperazine

A mixture of 84.2 g of 4-methanesulphonyl-2,2-dimethyl-1-nitrosopiperazine, 90.5 g of thiourea dioxide, 200 ml of ethanol and 200 ml of water is cautiously treated with 85 g of caustic soda and heated to reflux for 30 hours. After cooling, the mixture is filtered and the product is isolated from the filtrate by extraction with methylene chloride. After drying over sodium sulphate and concentrating the methylene chloride solution, the oil which remains is dissolved in a little ethanol and precipitated as the hydrochloride by addition of ethanolic hydrochloric acid.

Yield: 44 g, M.p.: 206° C. (dec.)

d) 3-(2,2-Dimethyl-4-methanesulphonylpiperazin-1-yl)sydnone imine hydrochloride A solution of 48 g of 1-amino-2,2-dimethyl-4-methanesulphonylpiperazine hydrochloride in 300 ml of water is cooled in an ice bath, treated with 12 g of sodium cyanide and adjusted to a pH of 7–7.5 by dropwise addition of conc. hydrochloric acid. 19 g of 39% strength formalin solution are then added and the pH of the mixture is kept at about 7 using sodium carbonate solution, the mixture being stirred at room temperature. After 2 hours, it is again cooled to 0°–5° C., 14 g of sodium nitrite are added and it is rendered acidic (pH=2.5–3) by dropwise addition of conc. hydrochloric acid. After 2 hours, the mixture is extracted by shaking with 200 ml of ethyl acetate and the org. phase is dried over Na$_2$SO$_4$. 100 ml of a conc. ethanolic hydrochloric acid are then added and the mixture is stirred in an ice bath for several hours. The precipitate is filtered off with suction, washed with ethyl acetate and dried.

Yield: 44.5 g, M.p.: 83°–5° C. (dec.)

The compounds of Examples 5 and 6 were obtained analogously to Example 1 by using tosyl chloride or dimethylaminosulphonyl chloride instead of methanesulphonyl chloride.

2) 3-(2,2-Dimethyl-4-tosylpiperazin-1-yl)sydnone imine hydrochloride

M.p.: 190°–92° C. (dec.)

3) 3-(2,2-Dimethyl-4-dimthylaminosulphonylpiperazin-1-yl)sydnone imine hydrochloride M.p.: 177-8° C. (dec.)

4) N-Nicotinoyl-3-(2,2-dimethyl-4-methanesulphonylpiperazin-1-yl)syndone imine 2 g of 8-(2,2-dimethyl-4-methanesulphonylpiperazin-1-yl)sydnone imine hydrochloride are added to an ice-cooled solution of 1.85 g of nicotinoyl chloride in 30 ml of pyridine. The mixture is then stirred at room temperature for 15 hours and cooled in an ice bath. The precipitate is filtered off with suction and recrystallised from ethanol.

Yield: 1.4 g, M.p.: 233° C. dec.

5) N-Butoxyacetyl-3-(2,2-dimethyl-4-methanesulphonylpiperazin-1-yl)sydnone imine Sodium bicarbonate (1.3 g) is added to an ice-cooled solution of 2 g of 3-(2,2-dimethyl-4-methanesulphonylpiperazin-1-yl)sydnone imine hydrochloride in 20 ml of water and a solution of 1 g of butoxyacetyl chloride in 30 ml of methylene chloride is then rapidly added dropwise.

After evolution of gas is complete, the organic phase is separated off, dried and evaporated in vacuo. The oil which remains is recrystallised from tert.butyl methyl ether.

Yield: 1.3 g, M.p.: 106°–8° C.

The following examples can be prepared analogously by use of the corresponding acid chlorides. 6) N-p-Anisoyl-3-(2,2-dimethyl-4-methanesulphonylpiperazin-1-yl)-sydnone imine M.p.: 210° C. (dec.)

7)
N-Ethoxycarbonyl-3-(2,2-dimethyl-4-methylsulphonyl-piperazin-1-yl)sydnone imine M.p.: 182° C. (dec.)

8)
N-Butoxycarbonyl-3-(2,2-dimethyl-4-methanesulphonylpiperazin-1-yl)sydnone imine M.p.: 164°-6° C.

9)
N-Isobutyroyl-3-(2,2-dimethyl-4-methanesulphonylpiperazin-1-yl)sydnone imine M.p.: 93°-6° C.

10)
N-Acetoxyacetyl-3-(2,2-dimethyl-4-methanesulphonyl-piperazin-1-yl)sydnone imine M.p.: 112°-114° C.

11)
N-Ethoxycarbonyl-3-(2,2-dimethyl-4-tosylpiperazin-1-yl)sydnone imine

M.p.: 157°-8° C.

12)
N-Ethoxycarbonyl-3-(2,2-dimethyl-4-dimethylaminosulphonylpiperazin-1-yl)sydnone imine M.p.: 132°-4° C.

13)
N-Cyclohexylcarbonyl-3-(2,2-dimethyl-4-methanesulphonylpiperazin-1-yl)sydnone imine M.p.: of the hydrochloride: 169° C. (dec.)

14)
N-Pivaloyl-3-(2,2-dimethyl-4-methanesulphonyloioerazin-1-yl)sydnone imine Oil, m.p. of the hydrochloride: 158°-9° C.

15)
N-(Pyrid-3-ylmethylcarbonyl)-3-(2,2-dimethyl-4-methanesulphonylpiperazin-1-yl)sydnone imine A mixture of 1,4 g of pyridyl-3-acetic acid and 30 ml of methylene chloride is treated with 1.4 ml of triethylamine and 1.25 ml of pivaloyl chloride with ice-cooling and the mixture is then stirred for 30 min. The reaction mixture thus obtained is added to an ice-cooled solution of 2.4 g of 3-(2,2-dimethyl-4-methanesulphonylpiperazin-1-yl)sydnone imine hydrochloride and 2.5 g of sodium bicarbonate in 20 ml of water and the mixture obtained is further treated as indicated in Example 5. The crude product obtained is recrystallised from water.

Yield: 1.5 g, M.p.: 73°-4° C.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. 3-Aminosydnone imines of the general formula I

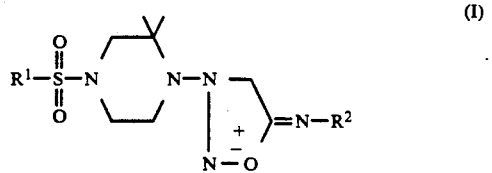

in which
R$^1$ denotes (C$_1$-C$_4$)-alkyl, di-(C$_1$-C$_4$)-alkylamino or (C$_6$-C$_{12}$)-aryl, which can optionally be substituted by (C$_1$-C$_4$)-alkyl;
R$^2$ denotes hydrogen or COR$^3$ and
R$^3$ denotes (C$_1$-C$_4$)-alkyl, (C$_1$-C$_4$)-alkoxy, (C$_1$-C$_4$)-alkoxy-(C$_1$-C$_4$)-alkyl, acetoxy(C$_1$-C$_4$)-alkyl, (C$_6$-C$_{12}$)-aryl, which can be substituted by (C$_1$-C$_4$)-alkyl or (C$_1$-C$_4$)-alkoxy, pyridyl, pyridyl(-C$_1$-C$_4$)-alkyl or (C$_3$-C$_8$)-cycloalkyl or a pharmacologically acceptable acid addition salt thereof.

2. 3-Aminosydnone imine according to claim 1, characterised in that R$^1$ denotes methyl, p-tolyl or dimethylamino.

3. 3-Aminosydnone imine according to claim 1, characterised in that R$^3$ denotes ethyl, i-propyl, tertbutyl, ethoxy, Pyridyl, P-methoxyphenyl or cyclohexyl.

4. Pharmaceutical preparation useful for the control and prevention of hypertension and/or angina pectoris, characterized in that it contains an effective amount of a 3-aminosydnone imine of the formula I according to claim 1, or a pharmacologically acceptable acid addition salt thereof as active compound together with pharmaceutically acceptable excipients and additives and, optionally, one or more other pharmacological active compounds.

5. Process of the control and prevention of hypertension and/or angina pectoris which comprises administering to a host in need thereof an effective dose of a substituted 3-aminosydnone imine of the general formula I according to claim 1, or a pharmacologically acceptable acid addition salt thereof.

* * * * *